(12) United States Patent
Hancock et al.

(10) Patent No.: US 11,759,256 B2
(45) Date of Patent: Sep. 19, 2023

(54) MICROWAVE ENERGY TRANSFER COMPONENT FOR ELECTROSURGICAL APPARATUS

(71) Applicant: CREO MEDICAL LIMITED, Chepstow (GB)

(72) Inventors: Christopher Paul Hancock, Bath (GB); Malcolm White, Chepstow (GB); Shaun Preston, Chepstow (GB)

(73) Assignee: CREO MEDICAL LIMITED, Chepstow (GB)

( * ) Notice: Subject to any disclaimer, the term of this patent is extended or adjusted under 35 U.S.C. 154(b) by 1190 days.

(21) Appl. No.: 16/328,662

(22) PCT Filed: Feb. 7, 2018

(86) PCT No.: PCT/EP2018/053098
§ 371 (c)(1),
(2) Date: Feb. 26, 2019

(87) PCT Pub. No.: WO2018/146160
PCT Pub. Date: Aug. 16, 2018

(65) Prior Publication Data
US 2020/0008872 A1    Jan. 9, 2020

(30) Foreign Application Priority Data
Feb. 13, 2017  (GB) ..................... 1702305

(51) Int. Cl.
*A61B 18/18*    (2006.01)
*A61B 18/00*    (2006.01)

(52) U.S. Cl.
CPC ............... *A61B 18/1815* (2013.01); *A61B 2018/00077* (2013.01); *A61B 2018/00101* (2013.01);
(Continued)

(58) Field of Classification Search
None
See application file for complete search history.

(56) References Cited

U.S. PATENT DOCUMENTS 4,621,642 A    11/1986  Chen
6,190,382 B1   2/2001   Ormsby et al.
(Continued)

FOREIGN PATENT DOCUMENTS

WO    WO 2013/121403 A1    8/2013

OTHER PUBLICATIONS

International Search Report and Written Opinion, issued by International Searching Authority in corresponding International Application No. PCT/EP2018/053098, dated Jun. 11, 2018.
(Continued)

*Primary Examiner* — Joanne M Rodden
*Assistant Examiner* — Nora W Rhodes
(74) *Attorney, Agent, or Firm* — ArentFox Schiff LLP

(57) ABSTRACT

A microstrip impedance transformer that permits efficient (i.e. low loss) coupling of a microwave feed line (e.g. a conventional 50Ω coaxial cable) to an instrument cable, where the instrument cable has a lower impedance (e.g. in the range 12 to 14Ω) and includes an internal passageway. The microstrip impedance transformer is configured to perform impedance matching between the microwave feed line and the instrument cable in a manner that does not adversely affect a separate feed, e.g. for delivering fluid, into the internal passageway.

20 Claims, 8 Drawing Sheets

(52) U.S. Cl.
CPC ............... *A61B 2018/00178* (2013.01); *A61B 2018/00577* (2013.01); *A61B 2018/00595* (2013.01); *A61B 2018/00755* (2013.01); *A61B 2018/1823* (2013.01); *A61B 2018/1892* (2013.01)

(56) References Cited

U.S. PATENT DOCUMENTS

| | | | |
|---|---|---|---|
| 6,463,336 B1* | 10/2002 | Mawhinney | A61N 5/04 600/15 |
| 2008/0015570 A1* | 1/2008 | Ormsby | A61B 18/1492 606/41 |
| 2011/0241794 A1 | 10/2011 | Pao et al. | |
| 2013/0072924 A1 | 3/2013 | Burgener et al. | |
| 2013/0252319 A1* | 9/2013 | Jung | G01N 33/54373 216/13 |
| 2013/0289557 A1 | 10/2013 | Hancock et al. | |
| 2015/0056107 A1* | 2/2015 | Hancock | A61L 2/24 422/186 |
| 2016/0058507 A1* | 3/2016 | Dickhans | A61B 18/1815 606/33 |
| 2016/0157934 A1* | 6/2016 | Kim | A61B 18/1815 606/33 |
| 2018/0296267 A1* | 10/2018 | Hancock | A61M 25/0084 |
| 2019/0083159 A1* | 3/2019 | Hancock | A61B 18/1477 |

OTHER PUBLICATIONS

Search Report under Section 17(5), issued by the United Kingdom Intellectual Property Office in counterpart United Kingdom Application No. GB1702305.2, dated Jun. 22, 2017.

* cited by examiner

MICROWAVE ENERGY TRANSFER COMPONENT FOR ELECTROSURGICAL APPARATUS

CROSS-REFERENCE TO RELATED APPLICATIONS

This application is a National Stage entry of International Application No.: PCT/EP2018/053098, filed Feb. 7, 2018, which claims priority to Great. Britain Patent. Application No. 1702305.2, filed Feb. 13, 2017. The disclosures of the priority applications are hereby incorporated in their entirety by reference.

TECHNICAL FIELD

The present application invention relates to electrosurgical apparatus comprising an electrosurgical instrument for non-invasive or percutaneous insertion to a treatment site to enable delivery of electromagnetic radiation to biological tissue. In particular, the application relates to means for efficiently coupling energy between an electrosurgical generator and the electrosurgical instrument.

BACKGROUND TO THE INVENTION

Electrosurgical instruments are used to deliver electromagnetic (EM) energy (in particular microwave and radiofrequency energy) to biological tissue, for purposes such as cutting and/or cauterising biological tissue.

Typically, apparatus for delivering EM energy to body tissue comprises a generator comprising a source of EM energy, and an electrosurgical instrument connected to the generator for delivering the energy to the biological tissue. EM energy is typically supplied to the electrosurgical instrument from the EM generator using a cable running from the generator to the instrument. Conventional cables used for this purpose have a coaxial transmission line structure comprising a solid cylindrical inner conductor, a tubular layer of dielectric material around the inner conductor, and a tubular outer conductor around the dielectric material. Such co-axial transmission lines have a nominal characteristic impedance ($Z_o$), typically either 50Ω or 75Ω.

The electrosurgical instrument may comprise a radiating portion, e.g. located at a distal tip. EM energy is transmitted along the coaxial cable and emitted from the radiating portion. Energy emitted from the radiating portion is delivered to biological tissue at the treatment site, e.g. to cause localised heating, or tissue cutting, or cauterisation/coagulation.

As EM energy traverses the electrosurgical instrument apparatus, it experiences impedance, i.e. opposition or resistance to the flow of energy. Changes in impedance may cause power loss and multiple reflections within the apparatus. Such reflections can cause unwanted heating of the apparatus.

To minimise power loss, reflections and heating effects, it is desirable to match impedance along the energy delivery pathway within the apparatus. In one example, impedance matching can be achieved by introducing impedance transformer structures within the energy delivery pathway.

U.S. Pat. No. 6,190,382 discloses an electrosurgical instrument for ablating biological tissue inside the atrium of a patient's heart. The instrument comprises a deployable monorail guide which precisely guides a radiofrequency emitting antenna to the correct treatment site. A microstrip section is included between two coaxial cables conveying the radiofrequency to the antenna.

SUMMARY OF THE INVENTION

At its most general, the present invention provides a microstrip impedance transformer that permits efficient (i.e. low loss) coupling of a microwave feed line (e.g. a conventional 50Ω coaxial cable) to an instrument cable, where the instrument cable has a lower impedance (e.g. in the range 12 to 14Ω) and may include an internal passageway. The microstrip impedance transformer is configured to perform impedance matching between the microwave feed line and the instrument cable in a manner that does not adversely affect a separate feed into the internal passageway.

According to the invention, there may be provided an electrosurgical apparatus comprising: a microwave feed line for carrying microwave electromagnetic (EM) energy having a frequency from an electrosurgical generator; an instrument cable for insertion into a patient's body to a treatment site, the instrument cable comprising: a coaxial transmission line for conveying the microwave EM energy, and an internal passageway for providing access to the treatment site; and a junction arranged to transfer the microwave EM energy between a distal end of the microwave feed line and a proximal end of the instrument cable, wherein the microwave feed line has a first impedance at the frequency of the microwave EM energy, wherein the instrument cable has a second impedance at the frequency of the microwave EM energy, the second impedance being lower than the first impedance, and wherein the junction comprises: a microstrip impedance transformer arranged to match the first impedance and the second impedance, and a hollow conduit in fluid communication with the internal passageway. The microstrip impedance transformer may be arranged to ensure that microwave EM energy is not coupled into the hollow conduit at the junction, e.g. by adopting the configuration set out below.

The term "conductive" is used herein to mean electrically conductive, unless the context dictates otherwise.

Herein, the terms "proximal" and "distal" refer to locations further from and closer to a treatment site respectively. Thus, in use the proximal end is closer to a generator for providing the microwave EM energy, whereas the distal end is closer to the treatment site, i.e. the patient.

An electrosurgical instrument may be any instrument, or tool, which is used during surgery and which utilises microwave EM energy during treatment. Herein, microwave EM energy may mean electromagnetic energy having a stable fixed frequency in the range 300 MHz to 100 GHz. Preferred spot frequencies for the microwave energy include 915 MHz, 2.45 GHz, 5.8 GHz, 14.5 GHz, 24 GHz, and 31 GHz. Frequencies above 1 GHz are preferred. 5.8 GHz may be most preferred frequency.

The microstrip impedance transformer may comprise a planar dielectric substrate having an upper surface and a lower surface on opposite sides thereof, a ground conductor layer on the lower surface, and a microstrip conductor layer on the upper surface. The dielectric substrate may be made form any suitable low loss material. Materials with a high dielectric constant (e.g. greater than 5) may be preferred in order to enable the junction to be compact. The microstrip conductor layer may be set back from the periphery of the upper surface of the dielectric substrate to constrain the microwave EM field substantially within a region defined by the upper surface.

The microstrip conductor layer may comprise a proximal microstrip track portion having a first width ($W_1$) and a distal microstrip track portion having a second width ($W_2$), wherein the second width is greater than the first width ($W_2 > W_1$).

The distal microstrip track portion may be arranged to function as a quarter wave impedance transformer, and may be coupled directly to the instrument cable. An electrical length of the distal microstrip track portion may be an odd multiple of a quarter wavelength of the microwave EM energy conveyed by the quarter wave microstrip impedance transformer. The physical length of this section may depend upon the effective dielectric constant and the spread of the fields both within the dielectric substrate and the air. The second width may be selected to make a characteristic impedance $Z_0$ of the distal microstrip track portion satisfy the equation:

$$Z_0 = \sqrt{Z_{in} Z_L}$$

where $Z_{in}$ is an impedance of distal microstrip track portion and $Z_L$ is an impedance of the instrument cable at the frequency of the microwave EM energy.

The dimensions of the dielectric substrate and ground conductor layer may be identical for both the proximal microstrip track portion and the distal microstrip track portion. The microstrip conductor layer need not be limited to only two microstrip track portions.

The proximal microstrip track portion may be configured to couple effectively to the microwave feed line. The first width may thus be selected to make a characteristic impedance of the distal microstrip track portion substantially equal to the impedance of the microwave feed line at the frequency of the microwave EM energy.

The coaxial transmission line in the instrument cable may comprise an inner conductor, an outer conductor and a dielectric material separating the inner conductor from the outer conductor. At a proximal end of the coaxial transmission line, the inner conductor may extend proximally from the dielectric material and outer conductor to overlie (and preferably physically contact) the distal microstrip track portion in order to electrically connect with it. The dielectric material may extend proximally from a proximal end of the outer conductor to overlie a gap between the microstrip conductor layer and a distal edge of the planar dielectric substrate. Preferably the dielectric material physically contacts the dielectric substrate in this region to prevent significant microwave EM field generation in this zone. The outer conductor may be electrically connected to the ground conductor layer.

Similarly, the microwave feed line may comprise a coaxial cable having a primary inner conductor electrically connected to the proximal microstrip track portion and a primary outer conductor electrically connected to the ground conductor layer. These connections may be made through a suitable connector, e.g. an SMA connector or the like.

The hollow conduit may be mounted on the microstrip conductor layer. For example, the hollow conduit may be a tube that curves away from the planar dielectric substrate as it extends away from the instrument cable. This configuration is particularly useful where the internal passageway is formed within the inner conductor of the coaxial transmission line, and hence access to the internal passageway inherently occurs in a region where energy is also coupled into or conveyed by the coaxial transmission line.

The microwave feed line and the instrument cable may be secured to the planar dielectric substrate at the junction. For example, the microwave feed line and the instrument cable may be secured to the planar dielectric substrate via conductive attachment elements that provide an electrical connection to the ground conductor layer.

In one example, the junction may comprise a conductive shield housing that surrounds the quarter wave microstrip impedance transformer. The shield housing may be a box or mesh encasing the junction. The shield housing may be grounded, e.g. electrically connected to the ground layer of the microstrip impedance transformer. The microwave feed line and the instrument cable may be secured to the quarter wave microstrip impedance transformer via the shield housing. The hollow conduit may extend through an aperture in the shield housing to provide access to the internal passageway.

The shielding around the transformer may be particularly advantageous for this structure as field lines (E and H) will radiate from the structure (due to the fact that the structure is asymmetrical and so field lines will couple into free space). The shielding may operate as a Faraday cage to prevent these fields coupling into other objects or causing interference to other equipment in the operating theatre or elsewhere. The shielding may be configured to ensure that the fields at the junction are not affected, i.e. unwanted modes such as 'box modes' are not set up.

BRIEF DESCRIPTION OF THE DRAWINGS

Examples of the invention are discussed in detail below with reference to the accompanying drawings, in which.

DETAILED DESCRIPTION; FURTHER OPTIONS AND PREFERENCES

Figure 1:
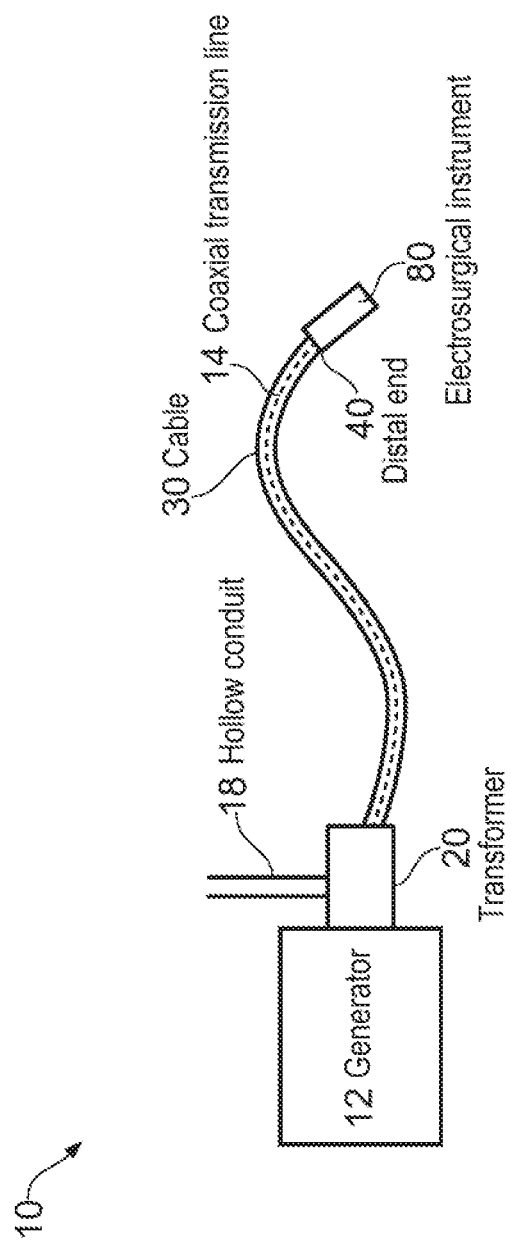
FIG. 1 is a schematic diagram of an electrosurgical apparatus that is an embodiment of the present invention.

FIG. 1 is a schematic diagram of an electrosurgical apparatus 10 that provides a context for the present invention.

The electrosurgical apparatus 10 comprises an EM generator 12 which generates EM energy (microwave and/or radiofrequency energy). The generator 12 is connected to a transformer 20. The transformer 20 is a microstrip impedance transformer 100, which is described in more detail with reference to FIGS. 2 to 4 below. The transformer 20 is located at a junction between the generator 12 and an energy conveying cable 30.

In this example the energy conveying cable 30 is a coaxial transmission line 14. The coaxial transmission line 14 comprises an inner conductor surrounded by a dielectric material that separates the inner conductor from an outer conductor. The coaxial transmission line 14 includes an internal passageway, e.g. within the inner conductor, for transporting materials, e.g. saline, or instruments along the cable 30. A hollow conduit 18 is connected to a proximal end of the cable 30 at the junction with the transformer 20. The hollow conduit 18 is in fluid communication with the passageway, and hence acts as a means for introducing materials or instruments into the passageway.

The energy conveying cable 30 is a flexible and steerable shaft comprising the coaxial transmission line 14 and passageway. The cable 30 is insertable into the body of a patient during surgery. The cable 30 can be configured to be suitable for non-invasive or percutaneous insertion into the body. The cable 30 may have an outer sheath made from a flexible biocompatible material.

The cable 30 extends away from the generator 12 and terminates at a distal end 40. An electrosurgical instrument 80 may be mounted or may protrude from the passageway at the distal end 40. The transmission line 14 is connected to the instrument 80 at the distal end 40. Electromagnetic (EM) energy (e.g. microwave EM energy) is transmitted from the generator 12 through the transformer 20 and delivered by the transmission line 14 to the instrument 80. The instrument may include a radiating tip arranged to emit the EM energy for absorption by surrounding biological tissue. The energy emitted from the radiating tip may ablate and/or cauterise the tissue.

The instrument 80 may also include an opening in fluid communication with the internal passageway of the coaxial transmission line 14. Materials introduced into the hollow conduit 18 by the operator are thus carried through the passageway within the cable 30 into the body of the patient, and can access a distal treatment zone through the opening.

The impedance transformer 20 between the generator 12 and the coaxial transmission line 14 of the cable 30 functions to match or improve the matching between an impedance of the generator 12 and an impedance of the coaxial transmission line 14. This prevents power loss and multiple reflections as the energy is introduced to the coaxial transmission line 14, and may thus prevent unwanted heating effects within the apparatus 10.

Figure 2B:
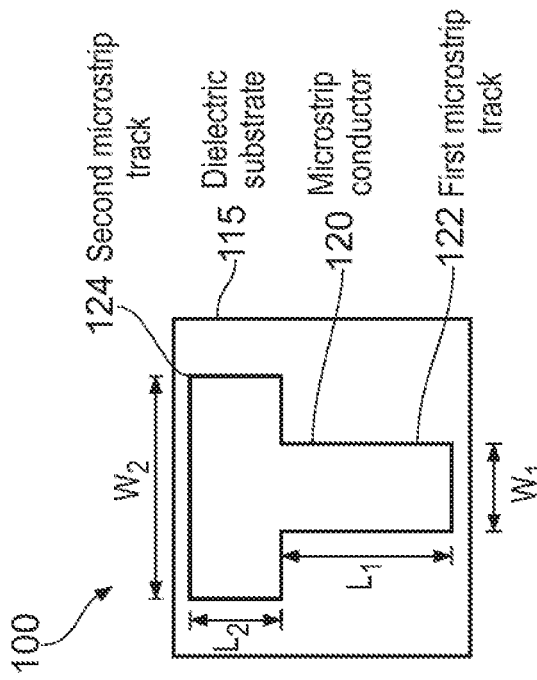
FIG. 2B is a schematic top view of the microstrip impedance transformer structure of FIG. 2A.
Figure 2A:
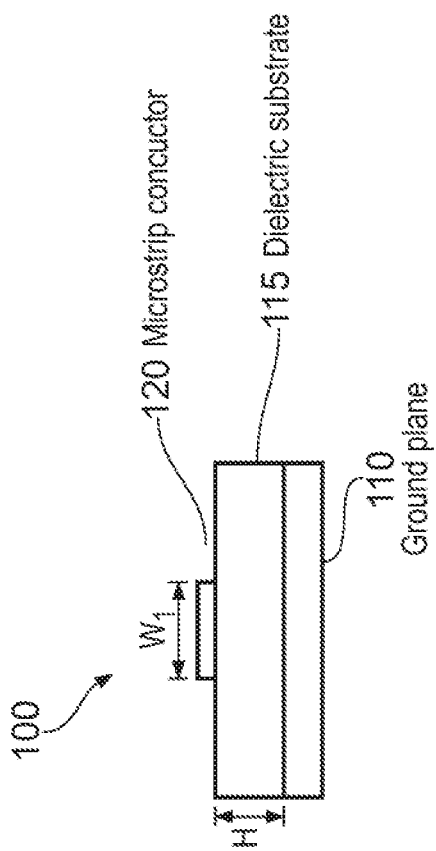
FIG. 2A is a schematic side view of a microstrip impedance transformer structure suitable for use in the invention.

FIGS. 2A and 2B are schematic diagrams of a microstrip impedance transformer structure 100 from the side and top respectively. The microstrip impedance transformer 100 is an electrical transmission line which can be fabricated using printed circuit board technology. The microstrip transformer structure 100 comprises three layers. A first layer is a conductive layer that provides a ground plane 110. A second layer is a dielectric substrate 115 on top of the ground plane 110. A third layer is a conductive layer fabricated on top of the dielectric substrate 115. The third layer is the active layer, and is referred to herein as a microstrip conductor layer 120.

The dielectric substrate 115 may be any dielectric material. As an example, Rogers Corporation TMM10 high frequency material may be used. Other substrate materials include glass reinforced with epoxy (commonly referred to as FR-4), and ceramic, e.g. alumina. The ground plane 110 and the microstrip conductor 120 may be fabricated from any conductive material, e.g. silver, gold, etc.

The microstrip conductor layer 120 has a width (W) which is measured in a direction perpendicular to the direction of travel of the EM energy from the generator 12, i.e. lateral to an axial direction of the coaxial transmission line 14. The impedance of the microstrip conductor layer 120 changes depending on this width. The characteristic impedance of the microstrip transformer 100 varies with the width of the microstrip conductor.

As shown in the top view of FIG. 2B, the microstrip conductor layer 120 comprises two track portions having different widths. In this example, a first (proximal, generator-side) microstrip track 122 has a width ($W_1$) which is narrower than a width ($W_2$) of a second (distal, cable-side) microstrip track 124. The geometry of the dielectric substrate 115 and the ground plane are identical for each track portion, so the first microstrip track 122 has a higher impedance value than the second microstrip track 124. In one embodiment, the first microstrip track 122 has a width ($W_1$) of 2.5 mm and the second microstrip track 124 has a width ($W_2$) of 6 mm, for example. As explained below, the width ($W_1$) may be selected to ensure that the first microstrip track has substantially the same impedance as the generator, and the width ($W_2$) may be selected to ensure that the second microwave track has an impedance that enables it to operate as a quarter wave impedance transformer. In another example, the width of the second microstrip track may be narrower that the first microstrip track. This configuration would be used if the instrument cable had a higher impedance than the generator.

Each track portion of the microstrip conductor 120 also has a length which is measured parallel to the direction of travel of the EM energy, i.e. along the axial direction of the coaxial transmission line 14. The first microstrip track 122 has a length ($L_1$) which is longer than a length ($L_2$) of the second microstrip track 124. In one example, the length $L_1$ is 10 mm, and the length $L_2$ is 2.5 mm. The length ($L_2$) may be substantially equal to an odd multiple of a quarter wavelength of the EM energy as it propagates within the microstrip structure. The length ($L_1$) may be selected by simulation or the like to ensure that the field shape of the transformer delivers the EM energy efficiently.

The dielectric substrate 115 has a width measured perpendicular and a length measured parallel to the direction of travel of the EM energy. The dielectric substrate may have a width of 20 mm and may have a length of 15 mm. The microstrip conductor layer 120 may thus be set back from a periphery of the dielectric substrate 115. In this embodiment the cable and SMA connector are attached with the use of solder. For this reason the conductor layer is set back to ensure that there is no breakdown/chance of solder flow connecting the conductive layer and the ground layer at the proximal end of the transformer. Due to the geometry of the SMA connector without this small gap, the outer of the connector would be in contact with the conductive layer and create a short.

Another parameter that can be used to control the impedance of the transformer structure is the thickness or height (H) of the dielectric substrate 115. The thickness dimension is perpendicular to the width (W) and length (L) dimensions of the microstrip conductor layer 120.

Figure 3:
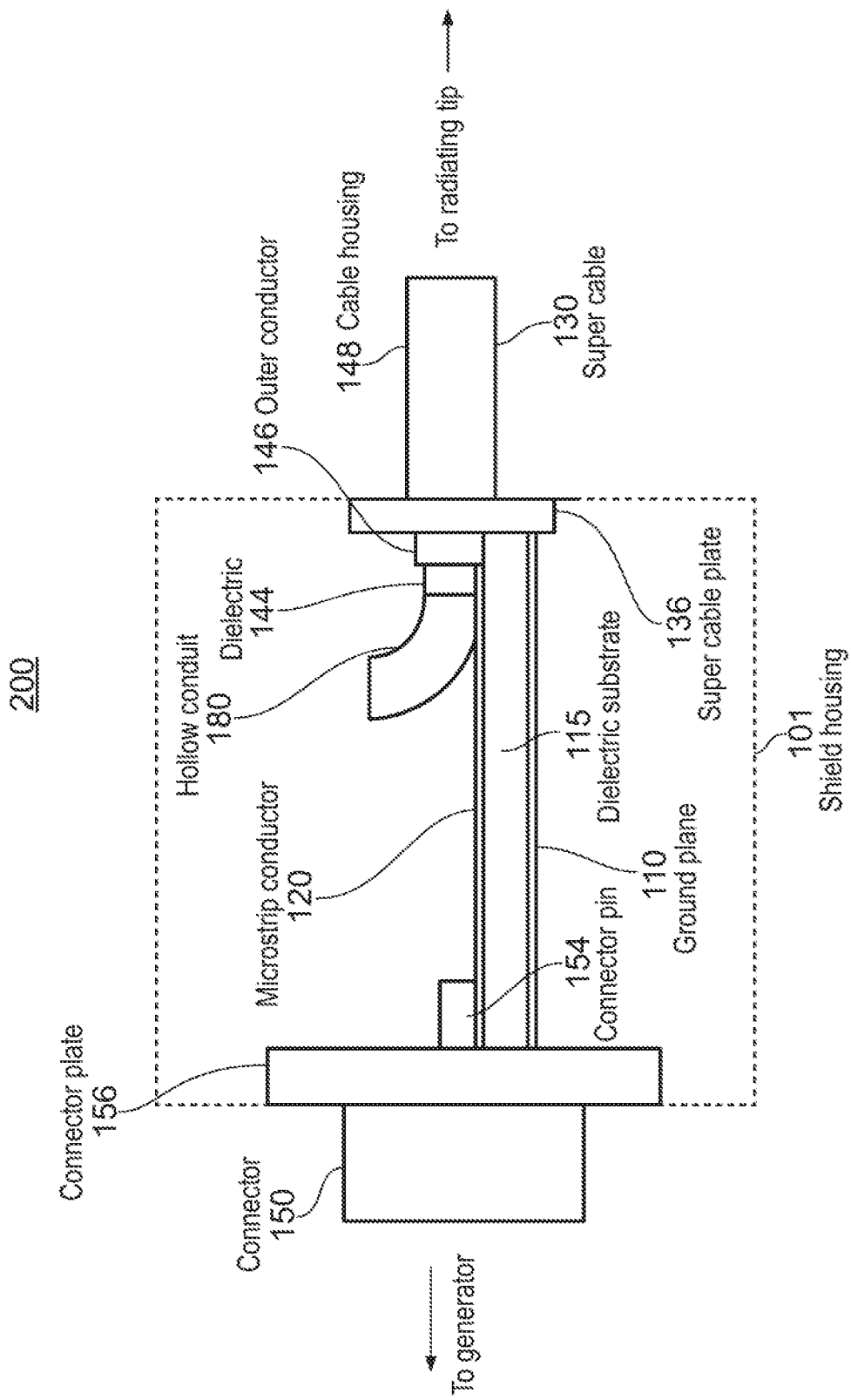
FIG. 3 is a schematic side view of a microstrip impedance transformer connected in an electrosurgical apparatus that is an embodiment of the present invention.
Figure 4:
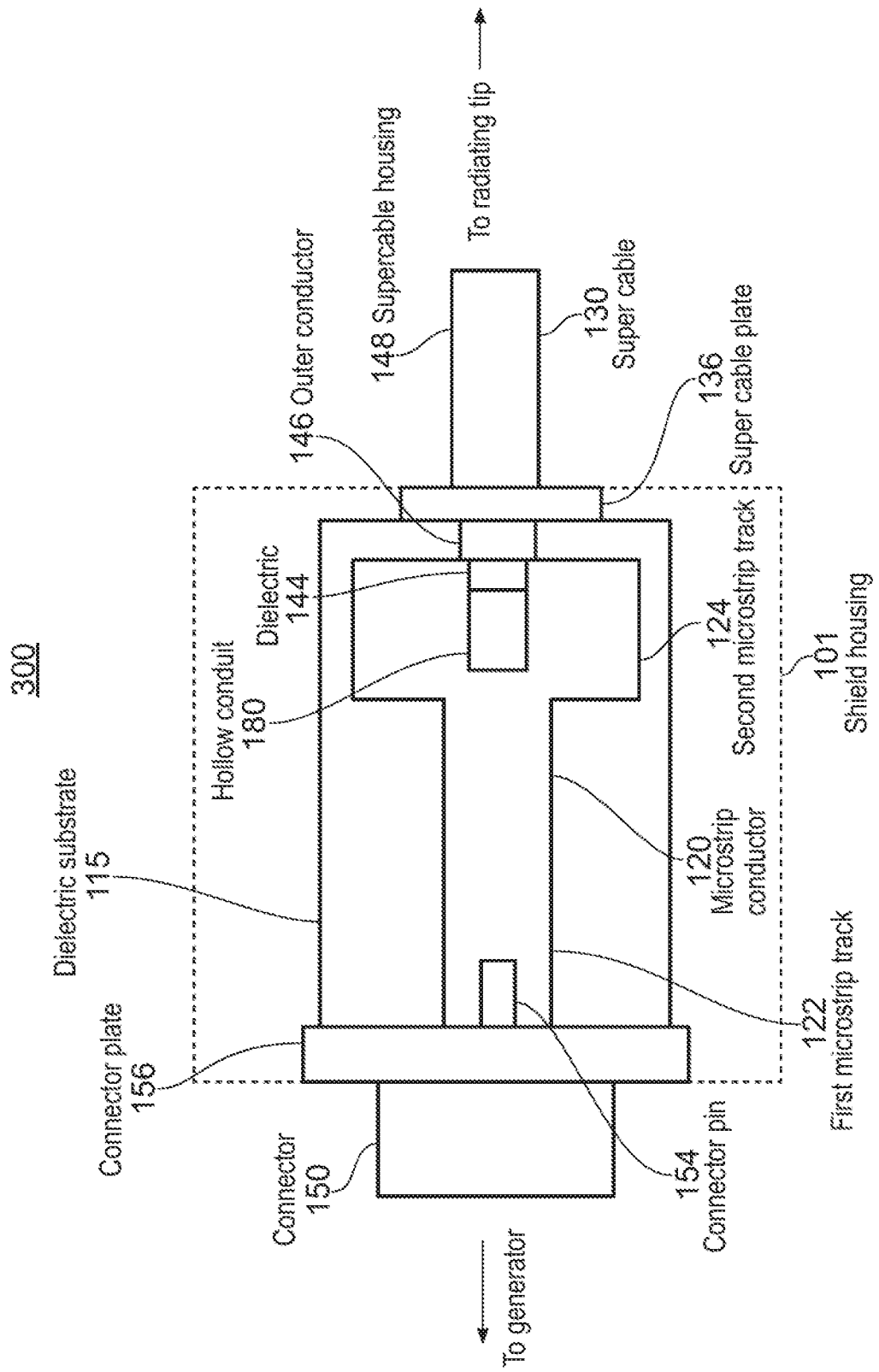
FIG. 4 is a schematic top view of the microstrip impedance transformer of FIG. 3.

FIGS. 3 and 4 are schematic side and top views respectively of a junction 200 between a generator (not shown) and an energy conveying cable 30. The junction comprises a microstrip transformer 100 as discussed above connected between a generator-side connector 150 and a proximal end of the coaxial transmission line that is conveyed by the cable 30. The same reference numbers are used for corresponding features, which are not described again.

The generator-side connector 150 is connected to the first microstrip track 122 at a proximal side of the microstrip transformer 100. The generator-side connector 150 may be any connector which can connect an EM energy generator 12 to a microstrip impedance transformer 100. For example, the connector 150 may be a standard SMA (SubMiniature version A) connector. The connector 150 has a central conductor pin 154 which is electrically connected (e.g. soldered) to the first microstrip track 122 of the microstrip impedance transformer 100.

The outer part (ground) of the connector 150 is connected to the ground plane 110 of the microstrip impedance transformer 100. One way to do this is to use a connector plate 156 which surrounds the outside of the connector 150 and is bonded directly to the ground plane 110, thus creating a connection between the outside of the connector 150 and the ground plane 110 of the microstrip impedance transformer 100. The connector plate 156 may be soldered or screwed to the ground plane 110.

The cable 30 is connected to the microstrip impedance transformer 100 at an end opposite to that of the generator 12. The inner conductor 144 and dielectric material 146 of the coaxial transmission line protrude proximally beyond a proximal end of the outer conductor (not shown). The inner conductor 144 and dielectric material 146 overlie the top surface of the microstrip transformer 100. The inner conductor 144 is electrically connected (e.g. bonded or soldered) to the second microstrip track 124 of the microstrip impedance transformer 100. The dielectric material 146 lies over the gap between the second microstrip track 124 and a distal edge of the substrate 115 to ensure that that inner conductor is isolated.

The outer conductor of coaxial transmission line is connected to the ground plane 110 of the microstrip impedance transformer 100. This can be done using a cable terminal plate 136, which surrounds the cable and is in electrical contact with the outer conductor. The plate 136 can be bonded e.g. soldered directly to the ground plane 110, creating a connection between the outer conductor of the transmission cable and the ground plane 110 of the microstrip impedance transformer 100.

Meanwhile, the hollow conduit 18 protrudes from a proximal end of the inner conductor 144 and curves up an away from the top surface of the microstrip transformer 100.

The electrosurgical instrument apparatus of FIGS. 3 and 4 operate as follows. EM energy is generated by the generator 12 which flows into the microstrip impedance transformer 100 by the connector 150. The EM energy travels from the connector pin 154 of the connector 150, and into the first microstrip track 122. The width of the first microstrip track 122 is chosen so that its impedance is similar to the impedance of the generator. The impedance of the generator may be approximately 50Ω. The EM energy then travels into the second microstrip track 124. The second microstrip track 124 is wider than the first microstrip track 122. The width of the second microstrip track 124 is chosen so that it has the correct impedance to act as a quarter wave impedance transformer. As discussed above, its length is selected to be an odd multiple of a quarter wavelength in order to match the impedance of generator impedance to the (lower) impedance of the cable 30.

The impedance of the cable 30 may be approximately 12 to 14Ω. As EM energy travels from the first microstrip track 122 into the second microstrip track 124, the impedance that it experiences reduces, from approximately 50Ω to approximately 12 to 14Ω for example. The microstrip impedance transformer 100 therefore matches the impedance of the generator 12 to the impedance of the transmission cable 14 running through the supercable 30.

Thus, where the frequency of energy delivered from the generator is f, the length $L_2$ of the second microstrip track may be calculated as $$L_2 = \frac{1}{4}\frac{c}{\sqrt{\varepsilon_{eff}}}$$

where c is the speed of light and $\varepsilon_{eff}$ is an effective dielectric constant at the junction, which depends on the geometry of the microstrip line and the relative permittivity $\varepsilon_r$ of the dielectric substrate and surrounding material (e.g. air) in a known manner.

And to ensure that the second microstrip track operates as a quarter wave impedance transformer, its width is selected to make its characteristic impedance $Z_0$ satisfy the equation:

$$Z_0 = \sqrt{Z_{in}Z_L}$$

where $Z_{in}$ is the generator impedance (50Ω in the example above) and $Z_L$ is the cable impedance (around 12Ω in the example above). In one example, the width of the second microstrip track is selected to make $Z_0$ around 24.5Ω.

In another embodiment, the connector plate 156 and cable terminal plate 136 may be integrated into a conductive shield housing 101 that completely surrounds the microstrip impedance transformer 100. The shielding can be made from copper. For example a 1 mm thick copper sheet that acts as a Faraday cage to prevent EM energy from escaping. The shielding can be a hollow cuboid with a length which is measured parallel to the direction of travel of the EM energy, a width which is measured perpendicular to the direction of travel of EM energy, and a height which is measured perpendicular to its width and the length. The shielding may have a length of 25 mm, a width of 22 mm and a height of 22 mm for example.

The inventor has found the configuration of the microstrip transformer disclosed herein provides extremely effective isolation for the hollow conduit 18 as it connects into the coaxial transmission line. This is particularly advantageous because it can prevent unwanted heating of the instruments and/or liquids that pass through the hollow conduit 18.

Figure 5:
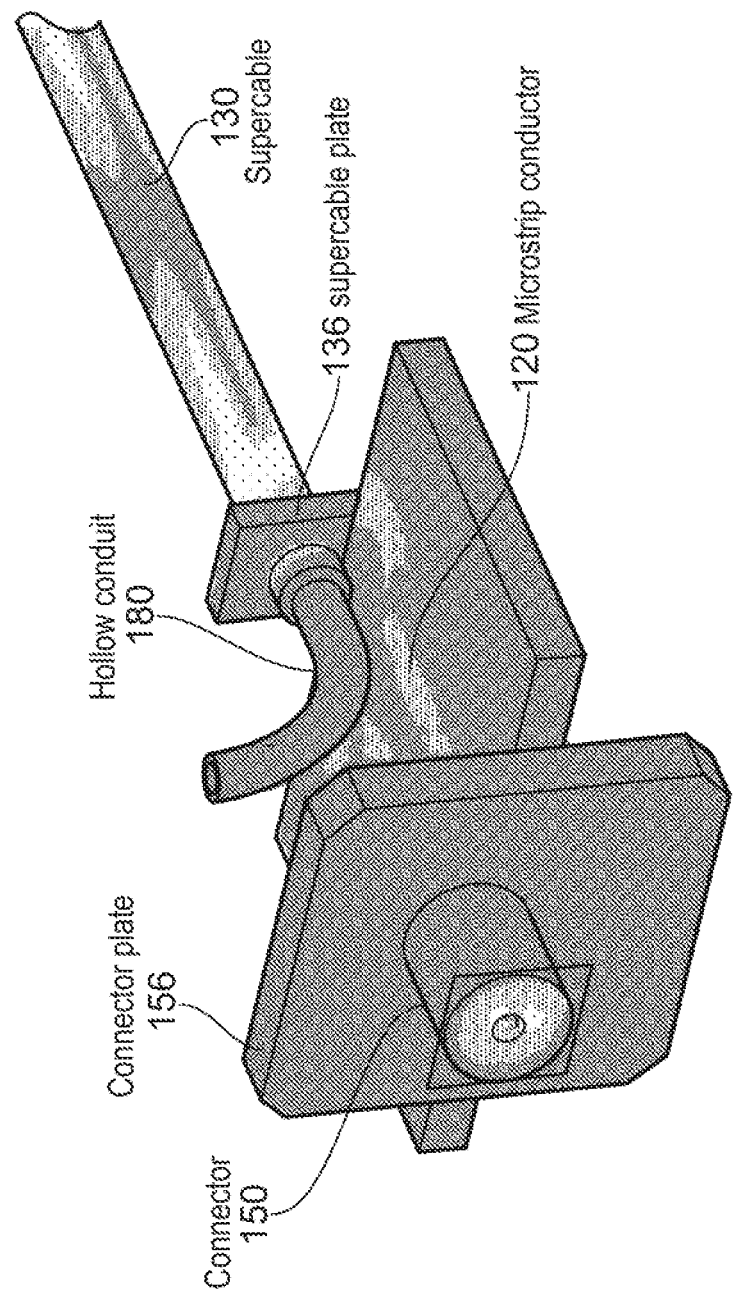
FIG. 5 is a simulated plot showing the electric field in the electrosurgical instrument apparatus of FIGS. 3 and 4.

FIG. 5 is a simulated plot showing the electric field in the apparatus. The lighter shades indicate stronger electric field, whereas the darker shades indicate weaker electric field. There is a strong electric field within the cable 30 and the microstrip impedance transformer 100, but there is minimal electric field present in the hollow conduit 18. This ensures that instruments and/or liquids present in the hollow conduit 18 do not experience unwanted heating effects due to the electric field. As an example, the hollow conduit 18 may contain a fluid such as saline. Saline is a good conductor of heat, so it is important for the hollow conduit to be isolated from the electric field which may induce heating.

Figure 6:
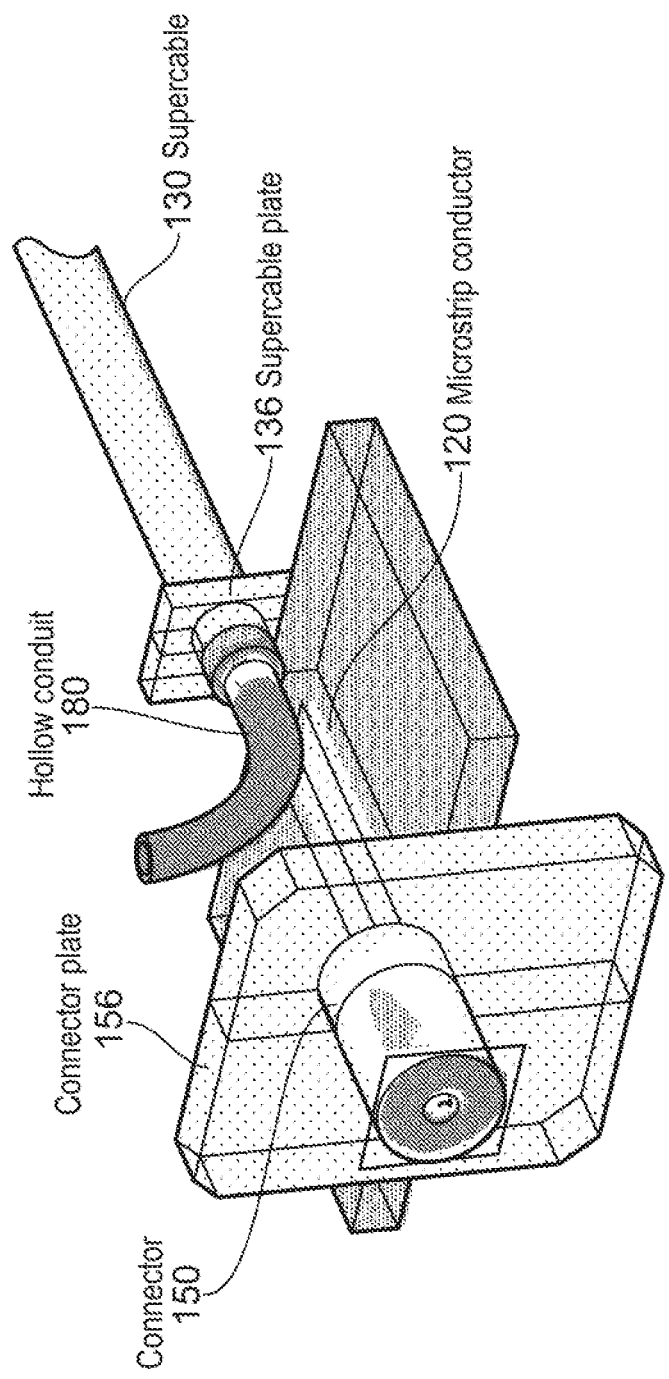
FIG. 6 is a simulated plot showing the power loss density in the electrosurgical instrument apparatus of FIGS. 3 and 4.

FIG. 6 is a simulated plot showing the power loss density in the apparatus. The lighter shades indicate high power loss and the darker shades indicated lower power loss. There is moderate power loss from the cable 30 and the microstrip impedance transformer 100, but minimal power is lost from the hollow conduit 18.

Figure 7:
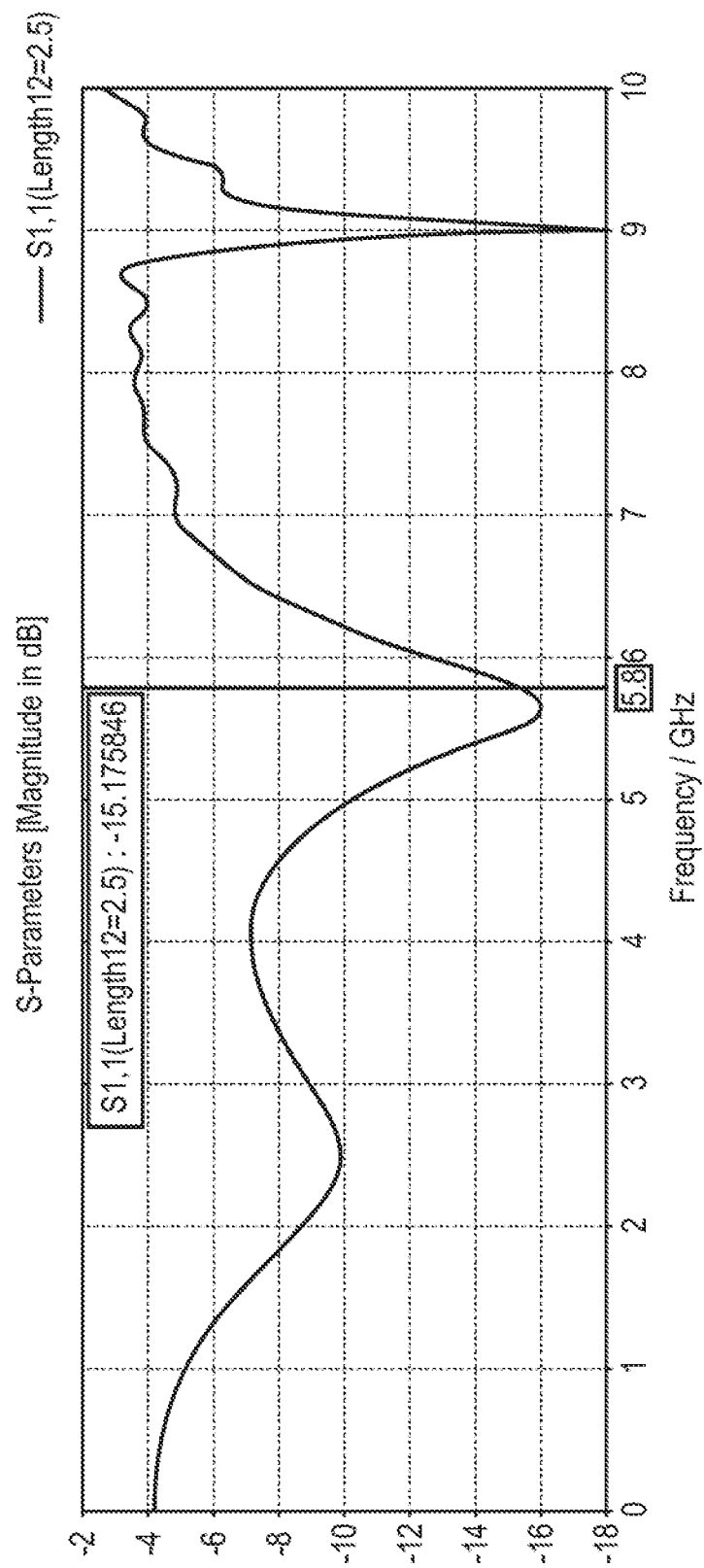
FIG. 7 is a graph showing a simulated return loss characteristic of the instrument apparatus of FIGS. 3 and 4 over a range of frequencies.

FIG. 7 is a graph showing a simulated return loss characteristic of the electrosurgical instrument apparatus of FIGS. 3 and 4 over a range of frequencies. It can be seen that there a low return loss around 5.8 GHz, which is the desired frequency for use and the frequency at which the transformer acts as a quarter wavelength transformer. The return loss at 5.8 GHz is −15 dB which means that around 96% of the power is delivered.

Figure 8:
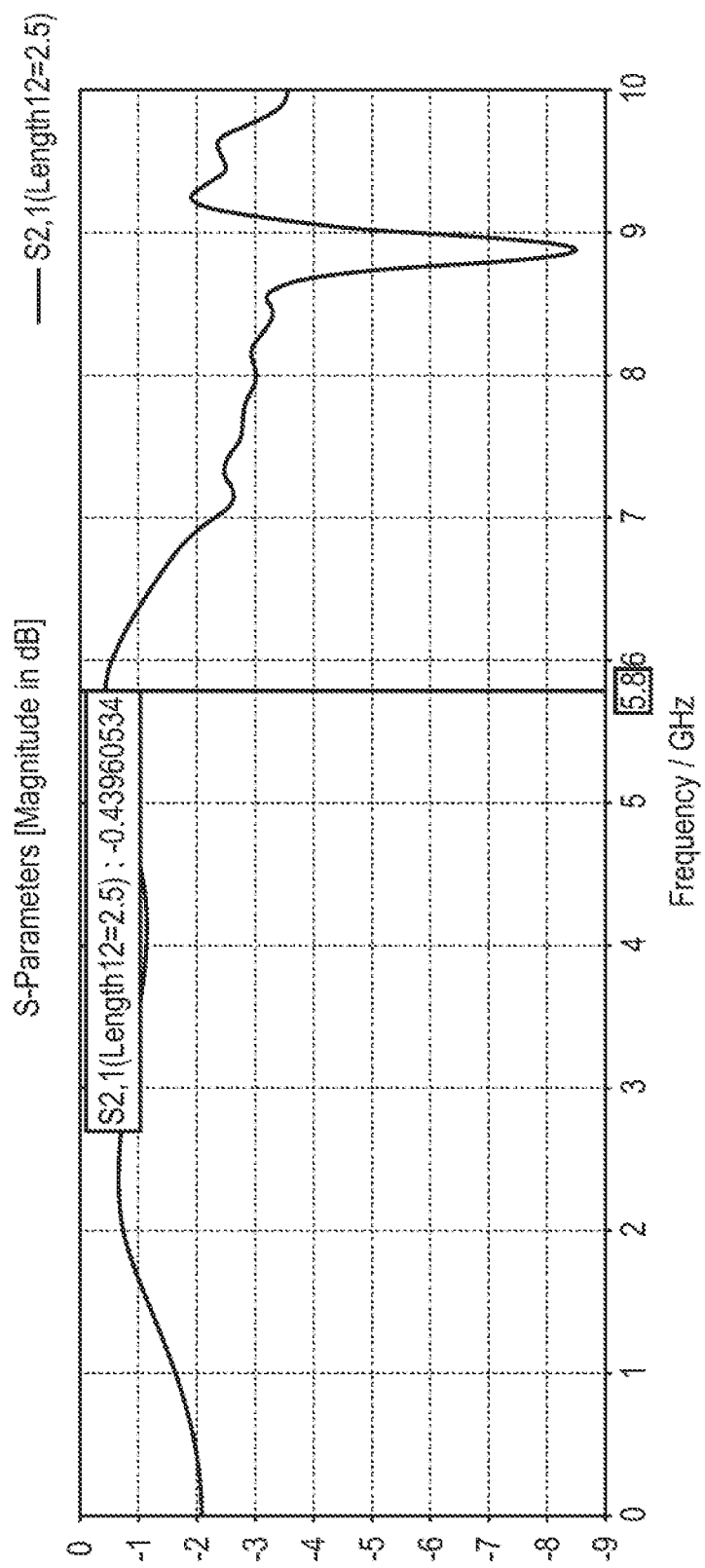
FIG. 8 is a graph showing a simulated insertion loss characteristic of the instrument apparatus of FIGS. 3 and 4 over a range of frequencies.

FIG. 8 is a graph showing a simulated insertion loss characteristic of the electrosurgical instrument apparatus of FIGS. 3 and 4 over a range of frequencies. It can be seen that there a low insertion loss around 5.8 GHz, which is the desired frequency for use. The insertion loss at 5.8 GHz is around 0.4 dB which means there is a loss of approximately 8.8%.

FIGS. 7 and 8 demonstrate that minimal energy is lost to reflections at the junction between the transformer and cable, which enables energy to be delivered efficiently into the coaxial transmission line without causing unwanted localised heating of other components.

The invention claimed is:

1. An electrosurgical apparatus comprising:
a microwave feed line for carrying microwave electromagnetic (EM) energy having a frequency from an electrosurgical generator;
an instrument cable for insertion into a patient's body to a treatment site, the instrument cable comprising:
a coaxial transmission line for conveying the microwave EM energy, and
an internal passageway for providing access to the treatment site; and
a junction formed between a distal end of the microwave feed line and a proximal end of the instrument cable, wherein the junction is configured to transfer the microwave EM energy directly between the distal end of the microwave feed line and the proximal end of the instrument cable,
wherein the microwave feed line has a first impedance at the frequency of the microwave EM energy,
wherein the instrument cable has a second impedance at the frequency of the microwave EM energy, the second impedance being lower than the first impedance, and
wherein the junction comprises:
a microstrip impedance transformer configured to match the first impedance and the second impedance, the microstrip impedance transformer being directly connected to the distal end of the microwave feed line and the proximal end of the instrument cable; and
a hollow conduit in fluid communication with the internal passageway for conveying fluid to the treatment site.

2. An electrosurgical apparatus according to claim 1, wherein the microstrip impedance transformer comprises:
a planar dielectric substrate having an upper surface and a lower surface on opposite sides thereof,
a ground conductor layer on the lower surface; and
a microstrip conductor layer on the upper surface,
wherein the microstrip conductor layer is set back from the periphery of the upper surface.

3. An electrosurgical apparatus according to claim 2, wherein the microstrip conductor layer comprises a proximal microstrip track portion having a first width ($W_1$) and a distal microstrip track portion having a second width ($W_2$), wherein the second width is greater than the first width ($W_2 > W_1$).

4. An electrosurgical apparatus according to claim 3, wherein an electrical length of the distal microstrip track portion is an odd multiple of a quarter wavelength of the microwave EM energy conveyed by the quarter wave microstrip impedance transformer.

5. An electrosurgical apparatus according to claim 3, wherein the second width is selected to make a characteristic impedance $Z_0$ of the distal microstrip track portion satisfy the equation:

$$Z_0 = \sqrt{Z_{in} \cdot Z_L}$$

where $Z_{in}$ is an impedance of distal microstrip track portion and $Z_L$ is an impedance of the instrument cable at the frequency of the microwave EM energy.

6. An electrosurgical apparatus according to claim 3, wherein the first width is selected to make a characteristic impedance of the distal microstrip track portion equal to the impedance of the microwave feed line at the frequency of the microwave EM energy.

7. An electrosurgical apparatus according claim 3, wherein the coaxial transmission line comprises an inner conductor, an outer conductor and a dielectric material separating the inner conductor from the outer conductor, and wherein, at a proximal end of the coaxial transmission line, the inner conductor extends proximally from the dielectric material and outer conductor to overlie the distal microstrip track portion, and the dielectric material extends proximally from a proximal end of the outer conductor to overlie a gap between the microstrip conductor layer and a distal edge of the planar dielectric substrate.

8. An electrosurgical apparatus according to claim 7, wherein the outer conductor is electrically connected to the ground conductor layer.

9. An electrosurgical apparatus according to claim 3, wherein the microwave feed line comprises a coaxial cable having an inner conductor electrically connected to the proximal microstrip track portion and an outer conductor electrically connected to the ground conductor layer.

10. An electrosurgical apparatus according to claim 2, wherein the hollow conduit is mounted on the microstrip conductor layer.

11. An electrosurgical apparatus according to claim 10, wherein the hollow conduit is a tube that curves away from the planar dielectric substrate as it extends away from the instrument cable.

12. An electrosurgical apparatus according to claim 2, wherein the microwave feed line and the instrument cable are secured to the planar dielectric substrate at the junction.

13. An electrosurgical apparatus according to claim 12, wherein the microwave feed line and the instrument cable are secured to the planar dielectric substrate via conductive attachment elements that provide an electrical connection to the ground conductor layer.

14. An electrosurgical apparatus according to claim 1, wherein the junction comprises a conductive shield housing that surrounds the quarter wave microstrip impedance transformer.

15. An electrosurgical apparatus according to claim 14, wherein the shield housing acts as a Faraday cage to confine EM fields emitted at the junction.

16. An electrosurgical apparatus according to claim 14, wherein the hollow conduit extends through an aperture in the shield housing.

17. An electrosurgical apparatus according to claim 14, wherein the microwave feed line and the instrument cable are secured to the quarter wave microstrip impedance transformer via the shield housing.

18. An electrosurgical apparatus according to claim 1, wherein the internal passageway is within the inner conductor of the coaxial transmission line.

19. An electrosurgical apparatus according to claim 1, wherein the second impedance is 12 to 14Ω.

20. An electrosurgical apparatus according to claim 1, wherein the frequency of the microwave EM energy is a stable fixed frequency selected from 5.8 GHz, 14.5 GHz, 24 GHz and 31 GHz.

* * * * *